United States Patent [19]

McDonald

[11] 4,395,311

[45] Jul. 26, 1983

[54] PREPARATION OF AMINOMETHANOLS

[75] Inventor: Charles J. McDonald, Midland, Mich.

[73] Assignee: The Dow Chemical Company, Midland, Mich.

[21] Appl. No.: 325,946

[22] Filed: Nov. 30, 1981

[51] Int. Cl.³ .......................... B01D 3/10; B01D 3/34
[52] U.S. Cl. ........................................ 203/34; 203/35; 203/91; 564/204; 564/497; 564/503
[58] Field of Search ....................... 564/497, 503, 204; 203/34, 35, 91

[56]         References Cited
        U.S. PATENT DOCUMENTS

| 2,139,123 | 12/1938 | Haas et al. | 564/497 |
| 2,139,124 | 12/1938 | Haas et al. | 564/497 |
| 2,395,281 | 2/1946 | Loder | 564/503 |
| 3,131,132 | 4/1964 | Moss et al. | 203/34 |
| 3,207,790 | 9/1965 | Glew et al. | 564/497 |
| 3,213,143 | 10/1965 | Fallstad | 564/497 |
| 3,402,203 | 9/1968 | Tindall | 564/503 |
| 3,429,925 | 2/1969 | Cour | 564/506 |
| 3,453,183 | 7/1969 | Okubo et al. | 564/497 |
| 4,166,828 | 9/1979 | McDonald | 564/204 |

FOREIGN PATENT DOCUMENTS 49-20110   2/1974   Japan .................... 564/497

Primary Examiner—Wilbur L. Bascomb, Jr.

[57]         ABSTRACT

Crude aminomethanols are converted to salt form by the addition of a strong acid and subsequently distilled under vacuum. The resulting purified aminomethanol is essentially free of unreacted aldehydes and other volatile impurities.

8 Claims, No Drawings

PREPARATION OF AMINOMETHANOLS

BACKGROUND OF THE INVENTION

This invention relates to an improved process for the preparation of aminomethanols.

N-(aminomethyl)-α,β-ethylenically unsaturated carboxamides may be prepared by carrying out an acid-catalyzed condensation reaction (Mannich reaction) of acrylamide, a secondary amine and a lower aldehyde, usually formaldehyde. See, for example, U.S. Pat. No. 4,166,828. Said carboxamides may be polymerized to form a cationic poly N-(aminomethyl)acrylamide which is useful as a flocculant in water and sewage treatment processes. The Mannich reaction of acrylamide is carried out either by simultaneously reacting the acrylamide, the amine and a lower aldehyde, or by prereacting the amine with the aldehyde. Both of the above processes are known in the art. See U.S. Pat. Nos 3,539,535 and 4,166,828.

In the above processes, unreacted aldehydes can react directly with the acrylamide, forming an N-methylol amide represented by the structure:

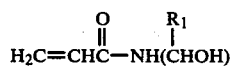
I.

wherein $R_1$ is hydrogen or an alkyl group having 1 or 2 carbon atoms. Under some conditions this by-product forms a methylene-bis-amide, an undesired cross-linking agent represented by the general structure:

II.

wherein $R_1$ is as described hereinbefore. Since cross-linking in the poly N-(aminomethyl)acrylamide decreases its solubility and hence its value as a flocculant, it is desirable to prepare the Mannich monomer free of cross-linking impurities.

Thus, careful control of the acid-catalyzed Mannich reaction of acrylamide monomer is desirable to minimize the formation of the undesired N-methylol amide and methylene-bis-amide. One method of controlling the reaction is by reacting the amine with the aldehyde to form an aminomethanol under basic conditions and then acidifying this reagent prior to introducing the acrylamide into the mixture. The formation of the undesired by-products is reduced in this manner, but unreacted aldehyde in the aminomethanol can still react with the acrylamide monomer to form cross-linking impurities. Thus, further improvement in the process can be achieved by removing the unreacted aldehyde from the aminomethanol prior to introducing of the acrylamide into the mixture. However, previously known methods of treating the aminomethanol to remove the unreacted aldehyde, such as by employing excess amine in the reaction or by heating the aminomethanol, leads to considerable degradation of the aminomethanol into useless and undesired by-products.

In view of the deficiencies of conventional processes of forming N-(aminomethyl)acrylamides, it is highly desirable to develop a process whereby aminomethanols are prepared in stable form with reduced amounts of unreacted aldehydes.

SUMMARY OF THE INVENTION

The present invention is such a desirable process for preparing aminomethanols. In this process, a reaction mixture containing an aminomethanol and a quantity of an unreacted lower aldehyde and/or other volatile impurities is treated with an acid of sufficient strength and quantity to protonate the aminomethanol. The aminomethanol is thereby converted to protonated form. The temperature of the reaction mixture is controlled during the acid-aminomethanol reaction in order to prevent thermal degradation of unreacted aminomethanol. When in protonated form, the aminomethanols have significantly increased thermal stability, which permits the removal of excess water, lower aldehydes and other volatile impurities by vacuum distillation. Therefore, upon completion of the reaction to protonate the aminomethanol, the reaction mixture is distilled under vacuum at a temperature at or below 85° C. and under sufficient vacuum to reduce the quantity of unreacted aldehyde present in the mixture. The product thus obtained may be reacted with polyacrylamide to form the desired Mannich product, which, when polymerized yields a polymer containing minimal amounts of cross-linked material, i.e., gels.

Alternatively, the aminomethanol is prepared in protonated form by (1) reacting a secondary amine with an acid of sufficient strength and quantity to protonate the amine, and (2) further reacting said protonated amine with a lower aldehyde to form the protonated aminomethanol. This reaction mixture is then distilled under vacuum as described above to remove unreacted aldehyde, and the purified aminomethanol so obtained may be reacted with acrylamide to form the desired Mannich product.

DETAILED DESCRIPTION OF THE INVENTION

The aminomethanol is prepared by reacting a lower aldehyde with a secondary amine. For the purposes of the present invention, the term "aminomethanol" is understood to mean a compound represented by the general formula:

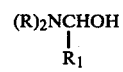
III.

wherein R is as described hereinafter and $R_1$ is a hydrogen or an alkyl group having 1 to 2 carbon atoms. Said definition also includes heterocyclic aminomethanols represented by the general formula:

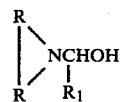
IV.

wherein the R groups are described hereinafter and $R_1$ is described hereinbefore.

The amine is a secondary amine, soluble in water or in acid solution, of the general formula:

V.

wherein each R is independently a hydrocarbyl or inertly substituted hydrocarbyl group or are both collectively a divalent hydrocarbon or ether which combines with N of the amine to form a heterocyclic ring compound represented by the formula:

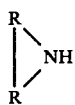

VI.

The R groups are selected such that the corresponding aminomethanol is soluble in acid. For the purposes of this invention, the term "inertly substituted hydrocarbyl group" means a hydrocarbyl group having a substituent group which is nonreactive under the conditions of the amine/aldehyde reaction and the subsequent aminomethanol-amide reaction. Particularly effective secondary amines include dimethylamine, diethylamine, diisopropylamine, $\beta$-histine, morpholine, piperidine, diallylamine and dimethanolamine. The Mannich product of an allyl or diallyl amine and acrylamide yields a monomer which polymerizes to a highly cross-linked polymer. Thus, if cross-linking is not desired in the ultimately-formed polymer, the use of allyl or diallyl amines is not preferred.

For the purposes of this invention, it is understood that the term "lower aldehyde" means aldehydes having 1 to 3 carbons and materials which will generate such lower aldehydes under the conditions of the process of this invention. Examples of aldehydes include formaldehyde, acetaldehyde and propionaldehyde with formaldehyde being preferred. Examples of materials containing or having the capability of generating aldehydes include paraformaldehyde, formalin and trioxymethane.

The molar ratio of amine to the lower aldehyde is chosen such that the equilibrium product mixture is predominantly the aminomethanol with minimum amounts of excess aldehyde, amine and other by-products. Excess amine leads to the predominance of diaminomethane while excess aldehyde leads to large amounts of unreacted aldehyde in the product. Preferably, the molar ratio of the amine to the lower aldehyde ranges from 0.66 to 1.33 moles of amine per mole of aldehyde. More preferably, from about 1 to 1.1 moles of the amine are used for each mole of the lower aldehyde.

The aminomethanols formed by the amine-lower aldehyde reaction have poor thermal stability. For example, dimethylaminomethanol degradation products of formic acid, trimethylamine and dimethylformamide are observed at significant levels after 24 hours at ambient temperatures. At 60° C., significant degradation products of dimethylaminomethanol are observed after only two hours. Since the reactions of lower aldehydes with amines are exothermic, the temperature of the reaction mixture is controlled so as to minimize thermal degradation of the aminomethanol as it forms. On the other hand, formaldehyde exists primarily as a polymer and must be thermally depolymerized to carry out the reaction with the amine. Therefore, if the lower aldehyde used in preparing the aminomethanol is formaldehyde, a means for maintaining the reaction temperature at a point sufficient to depolymerize the formaldehyde yet sufficiently low as to minimize the thermal degradation of the aminomethanol is employed. Said temperature control is achieved by controlling the rate of mixing the reactants or by employing any suitable means of removing heat from the reaction mixture. Said means of removing heat from the reaction mixture are well-known to those skilled in the art. Preferably, the temperature of the reaction mixture is maintained between 30° and 70° C. More preferably, the reaction temperature is maintained between 40° and 50° C.

Protonation of the aminomethanol is effected using an acid of sufficient strength to protonate the amino group. Examples of such acids are sulfonic acid and strong mineral acids such as sulfuric, nitric or hydrochloric. Of these, hydrochloric acid is most preferred because it may be introduced into the reaction mixture as a gas, thus reducing the amount of unnecessary water in the system.

The acid is added in an amount sufficient to essentially complete the protonation of the aminomethanol. Essentially complete protonation of the aminomethanol is achieved when the pH is adjusted into the range of 1 to 5. Preferably, the pH of the reaction mixture is adjusted to 2 to 4.

As an alternative to protonating the aminomethanol, the acid may be added to the amine prior to the reaction of the amine with the aldehyde. As described above, acid of sufficient strength and quantity is added so as to protonate the amine. The amine is thereby converted primarily to the salt form, which may be reacted with a lower aldehyde as described above to form the aminomethanol in salt form. This process is less preferred, however, because under these conditions the amine reacts more slowly with the aldehyde than does the nonprotonated amine. Moreover, this alternative process yields a lower proportion of the desired aminomethanol than does the reaction involving the nonprotonated amine.

The addition of acid to the aminomethanol forms the salt of the aminomethanol according to the equation:

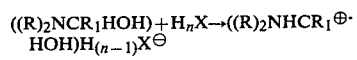

wherein R and $R_1$ are as described above, and n is 1, 2 or 3. Said aminomethanol salt (protonated aminomethanol) is more thermally stable than the corresponding unprotonated aminomethanols, and withstands somewhat higher temperatures without significant degradation. Thus, lower aldehydes, water and other volatile impurities are removed from the aminomethanol by vacuum distillation techniques well-known to those skilled in the art. In general, specific numerical temperature and vacuum levels are not critical as long as said temperature and vacuum are sufficient to remove unreacted aldehyde, excess water and other volatile impurities from the system. However, temperatures below about 85° C. are preferred to minimize potential degradation of the protonated aminomethanols. On the other hand, removal of the aldehyde and other volatile impurities is slowed at temperatures below about 40° C. Preferably, distillation is effected at temperatures of about 50° to 75° C., while increasing the vacuum until unwanted volatile impurities are removed.

The amount of unreacted aldehyde in the reaction mixture is significantly reduced by the practice of this invention. After distillation, the purified aminomethanol contains less than 1 percent by weight free formaldehyde. Any suitable means for detecting the presence of unwanted impurities in the reaction mixture may be employed to monitor the removal of said impurities.

The resulting aminomethanol may be reacted with acrylamide monomer to form the desired N-(aminomethyl)-α,β-ethylenically unsaturated carboxamide of the formula:

wherein R and $R_1$ are as described hereinbefore. This reaction proceeds with reduced amounts of the undesired aldehyde-induced cross-linking agents described above. The Mannich product thus formed may then be polymerized to form the desired N-aminomethyl carboxamide polymers. These processes are fully described in U.S. Pat. No. 4,166,828.

Alternatively, the aminomethanol produced in the practice of the present invention may be reacted directly with polyacrylamide to form the desired cationic carboxamide polymers.

The following examples are given to illustrate the invention and should not be construed as limiting the scope thereof. Unless otherwise indicated, all parts and percentages of these examples are by weight.

EXAMPLE 1

Into a 500 ml round bottom, three-neck flask equipped with a magnetic stirrer, dry ice condenser and dropping funnel is placed 137 parts of a 37 percent formaldehyde solution. To this is added over a period of 1½ hours 200.7 parts of a 40 percent dimethylamine solution by means of a dropping funnel. An ice bath is used to maintain the reaction exotherm below 45° C. To facilitate adding the gaseous acid the apparatus is modified to include a pH electrode and an inlet tube. Gaseous hydrochloric acid is then introduced to the flask over a period of two hours. During this process the temperature is maintained around 20° C. with an ice bath. The product is 31.7 percent solids and has a pH of 2.5.

One hundred forty-six grams of the reaction mixture containing protonated dimethylaminomethanol thus formed, which is 31.7 percent solids, is placed into a 200 ml distilling apparatus equipped with a magnetic stirrer, thermometer and small condenser. A vacuum is applied as indicated in Table I and the data collected as the distillation proceeds is reported in Table I.

TABLE I

| Time (min.) | Temperature (°C.) | Pressure (mm Hg) | Amt. H2O Removed (g) |
| --- | --- | --- | --- |
| 0 | — | — | — |
| 17 | 67 | 200 | condensation begins |
| 40 | 67 | 170 | — |
| 69 | 70 | 147 | 23.6 |
| 104 | 70 | 122 | 39.3 |
| 122 | 70 | 95 | 47.9 |
| 132 | 70 | 60 | 54.9 |
| 145 | distillation concluded | distillation concluded | 57.3 |

The final product weighs 75 grams and is calculated to be 62.0 percent solids. CMR spectra indicate that no residual formaldehyde is present. CMR spectral data indicate that the composition of the product after vacuum treatment includes the following species in salt form:

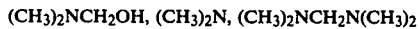

EXAMPLE 2

A quantity of protonated dimethylaminomethanol, 37.6 percent solids, is prepared according to the procedure described in Example 1. This product is distilled at 50° C. with a vacuum of about 50 mm Hg until the solid level is increased to 43.0 percent. CMR spectroscopy of the final product indicates no detectable amounts of formaldehyde or methanol.

What is claimed is:

1. A process for the purification of a reaction mixture containing an acid-soluble aminomethanol, and an unreacted aldehyde having 1 to 3 carbon atoms, said aminomethanol being represented by the general formula:

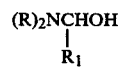

wherein $R_1$ is hydrogen or an alkyl group having 1 or 2 carbon atoms and each R is independently hydrocarbyl or inertly substituted hydrocarbyl or both R groups are collectively a divalent hydrocarbon or ether radical which combine with the nitrogen of the aminomethanol to form a heterocyclic ring represented by the formula:

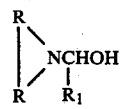

said process comprising the steps of:
 (a) contacting the reaction mixture with an acid of sufficient strength and quantity to effect protonation of the aminomethanol under conditions such that essentially all of the aminomethanol is protonated, and
 (b) distilling the acidified reaction mixture under reduced pressure under conditions including a temperature at or below 85° C. such that the amount of said unreacted aldehyde in the reaction mixture is reduced.

2. The process of claim 1 wherein the aminomethanol is the reaction product of formaldehyde and an amine selected from the group consisting of dimethylamine, diethylamine, diisopropylamine, β-histine, morpholine and piperidine.

3. The process of claim 1 wherein the acid is selected from a group consisting of hydrochloric acid, sulfuric acid and nitric acid.

4. The process of claim 2 wherein the aminomethanol is dimethylaminomethanol and the acid is hydrochloric acid.

5. A process for the preparation and purification of aminomethanols, said process comprising the steps of:
 (a) reacting (i) an acid-soluble secondary amine represented by the formula: $(R)_2NH$ wherein each R is independently hydrocarbyl or inertly substituted hydrocarbyl or both R groups are collectively a divalent hydrocabon or ether radical which combine with the nitrogen of the amine to form a heterocyclic ring represented by the formula:

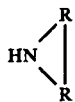

such that the corresponding aminomethanol is soluble in aqueous acid, with (ii) an acid of sufficient strength and quantity to effect protonation of the amine under conditions such that essentially all of the amine is protonated then (b) contacting the protonated amine with an aldehyde having 1 to 3 carbon atoms under conditions sufficient to cause reaction of the amine with said aldehyde to form at least 10 mole percent of the protonated aminomethanol based on moles of said aldehyde reactant, and then (c) distilling the reaction mixture under reduced pressure and under conditions including a temperature at or below 85° C. such that the amount of unreacted aldehyde in the reaction mixture is reduced.

6. The process of claim 5 wherein the amine is selected from the group consisting of dimethylamine, diethylamine, diisopropylamine, β-histine, morpholine and piperidine.

7. The process of claim 5 wherein the acid is selected from the group consisting of hydrochloric acid, sulfuric acid and nitric acid.

8. The process of claim 5 wherein the aldehyde is formaldehyde, the amine is dimethylamine and the acid is hydrochloric acid.

* * * * *